(12) United States Patent
Siqueira et al.

(10) Patent No.: US 9,199,957 B2
(45) Date of Patent: Dec. 1, 2015

(54) 2.5-FURANDICARBOXYLIC ACID INTEGRATED PRODUCTION PROCESS

(71) Applicant: PETROLEO BRASILEIRO S.A.-PETROBRAS, Rio de Janiero, RJ (BR)

(72) Inventors: Bernardo Galvao Siqueira, Rio de Janeiro (BR); Raphael Bezerra De Menezes, Rio de Janeiro (BR); Carlos Rene Klotz Rabello, Rio de Janeiro (BR); Marlito Gomes, Jr., Petropolis (BR)

(73) Assignee: PETROLEO BRASILEIRO S.A.-PETROBRAS, Rio de Janeiro (BR)

( * ) Notice: Subject to any disclaimer, the term of this patent is extended or adjusted under 35 U.S.C. 154(b) by 31 days.

(21) Appl. No.: 14/345,081

(22) PCT Filed: Oct. 17, 2013

(86) PCT No.: PCT/BR2013/000425
§ 371 (c)(1),
(2) Date: Mar. 14, 2014

(87) PCT Pub. No.: WO2015/054756
PCT Pub. Date: Apr. 23, 2015

(65) Prior Publication Data
US 2015/0274686 A1    Oct. 1, 2015

(30) Foreign Application Priority Data

Dec. 21, 2012  (BR) .......................... 10 2012 032839

(51) Int. Cl.
*C07D 307/68*    (2006.01)

(52) U.S. Cl.
CPC .................................... *C07D 307/68* (2013.01)

(58) Field of Classification Search
CPC ...................................................... C07D 307/68
USPC ......................................................... 549/485
See application file for complete search history.

(56) References Cited

U.S. PATENT DOCUMENTS 4,590,283 A    5/1986   Gaset et al.
7,572,925 B2   8/2009   Dumesic et al.

FOREIGN PATENT DOCUMENTS

WO    2008/053284 A1    5/2008

*Primary Examiner* — Taofiq A Solola
(74) *Attorney, Agent, or Firm* — Sughrue Mion, PLLC

(57) ABSTRACT

A two-step 2.5 FDCA integrated production process is described, comprising a first step for generating 5-HMF from streams comprising an aqueous carbohydrate solution wherein sub-critical water works as a catalyst by dehydrating the carbohydrates and generating 5-HMF, and a second step wherein 5-HMF is oxidized into 2.5 FDCA.

10 Claims, 2 Drawing Sheets
(2 of 2 Drawing Sheet(s) Filed in Color)

2.5-FURANDICARBOXYLIC ACID INTEGRATED PRODUCTION PROCESS

CROSS REFERENCE TO RELATED APPLICATIONS

This application is a National Stage of International Application No. PCT/BR2013/000425 filed Oct. 17, 2013, claiming priority based on Brazilian Patent Application No. 10 2012 032839-9 filed Dec. 21, 2012, the contents of all of which are incorporated herein by reference in their entirety.

BACKGROUND OF THE INVENTION

The present invention relates to the field of integrated processes for producing 2.5 FDCA (2.5-furandicarboxylic acid) from renewable-source carbohydrates. More specifically, related to a production process for 2.5 FDCA comprising two steps, a first step for producing 5-HMF via aqueous-phase carbohydrate dehydration, and a second step wherein 5-HMF is oxidized into 2.5 FDCA.

DESCRIPTION OF RELATED ART

Using renewable raw material resources for producing fuel and petrochemical products has been growing rapidly in the last few years, driven by society's demand for environmentally friendly products and processes.

In this context, one of the biggest challenges faced by the petrochemical industry is to develop productive compounds and processes that allow replacing fossil-based raw materials when producing worldwide consumer goods. A leading polymer is paraxylene-originated terephthalic acid used for producing polyesters (for example, polyethylene terephthalate (PET)); and benzene-originated styrene, which is the monomer used for producing polystyrene; and also, aromatic amides for producing polyaramides and aromatic isocyanates for producing polyurethanes.

Recent research has shown that 2.5-furandicarboxylic acid (2.5 FDCA. the English acronym) is a renewable resource compound that can replace terephthalic acid for producing polymers.

Currently, the most common route for producing 2.5 FDCA is through 5-hydroxymethylfurfural (5-HMF) oxidation, which in turn is traditionally produced by dehydrating hexoses, especially fructose.

Synthesis of 5-HMF is the limiting step for the 2.5 FDCA production process because 5-HMF is an unstable compound that may undergo re-hydration in aqueous phase, thereby originating undesirable byproducts such as levulinic and formic acid, or even condensate into polymers called humins.

Different alternatives have been studied to improve 5-HMF yields.

For example, U.S. Pat. No. 4,590,283 describes a process for producing 5-HMF wherein a feed stream containing fructose dissolved in dimethylsulfoxide (10% m/m-50% m/m) is brought into contact with a bed comprising an acid resin at a temperature of 70° C.-80° C. in the presence (counter-current) of an organic extracting solvent such as MIBK (isobutyl methyl ketone). The 5-HMF that is generated is extracted by MIBK, and the end of the process leads to yields of 97% mole/mole.

However, the disadvantage of that process is that it is difficult to separate the desired product, 5-HMF, from the solvents, in this case dimethylsulfoxide (DMSO) and MIBK, and there is also a chance of formation of toxic compounds from degradation of the solvents.

If a solvent with a lower boiling point than DMSO is used for extraction, an option presented in U.S. Pat. No. 4,590,283, large volumes of solvent are needed to make the extraction process efficient, which makes the entire process extremely expensive.

Another option is to use ionic liquids to assist in the production of 5-HMF as presented in patent document WO 2008/053284; however, this option has the disadvantage of the need of subsequent separation processes to recover both the ionic liquids and 5-HMF, which is expensive.

Biphasic routes have also been widely studied. In this case, the saccharide that has been dissolved in water is kept into contact with an acid catalyst and an organic extracting solvent such as MIBK. As the saccharide dehydration takes place in the aqueous phase, the 5-HMF that is formed migrates into the organic phase, thus avoiding re-hydration thereof.

U.S. Pat. No. 7,572,925 describes the use of modifiers in both the aqueous phase and the organic phase to optimize extraction of 5-HMF. Using a modified aqueous phase with DMSO (H2O:DMSO 4:6) on 10% glucose (m/m) and pH 1.0 (HCl as a catalyst), an organic phase comprised by MIBK:2-butanol 7:3 at 170° C., a 43% glucose conversion (mole/mole) and a 53% (mole/mole) 5-HMF selectivity could be achieved. Once again, in this case, 5-HMF must be separated from the phase in which the extraction is performed.

Therefore, one can see that all the known routes to separate the 5-HMF generated for later oxidation is a recurring difficulty.

Because oxidation of 5-HMF normally takes place in an aqueous phase, the most convenient solvent for an integrated process would be water. In addition, water allows for high carbohydrate solubility, especially of saccharides, which would allow operation in higher-concentration solutions, in addition to being inexpensive and causing no problems for the environment or human health.

However, the key disadvantages of carbohydrate dehydration in aqueous phase is the need to use equipment with special materials since mineral acids are used as catalysts, and the need of humin deactivation when heterogeneous catalysts are used, in addition to low 5-HMF yields in both cases.

Using sub-critical water such as described in the present invention solves the problems related to homogenous and heterogeneous acid catalysts because no special materials are required in the reactor and there are no heterogeneous catalysts that need to be deactivated. Ion product of sub-critical water is a few orders of magnitude higher than that of water at room temperature. This allows that the generated H+ ions to catalyze dehydration reactions. Furthermore, OH— ions also generated in this dissociation can catalyze isomerization reactions. This means that if a more inexpensive raw material such as glucose is used, part of the molecule will be isomerized into fructose, which is more reactive and provides a higher selectivity to 5-HMF.

Therefore, there is an unmet need in the art for integrated processes to produce 2.5 FDCA from aqueous carbohydrate solutions wherein the step of obtaining 5-HMF is conducted in aqueous phase, with high selectivity greater than 60% mole/mole, depending on the operational conditions and the raw material used, and without using organic solvents to recover 5-HMF, which reduces 5-HMF losses and has a positive impact on health and environment.

SUMMARY OF THE INVENTION 10

In general, the present invention relates to an integrated process for producing 2.5 FDCA from aqueous saccharide solutions.

The process comprises two main steps, a first step wherein saccharides, preferably hexoses, undergo aqueous-phase dehydration leading to the formation of 5-HMF, and a second step where 2.5 FDCA is formed from 5-HMF via oxidation reaction.

In the dehydration step within this process, the water comprising the reaction phase is in sub-critical state, therefore acting as a catalyst, thereby reaching selectivity greater than 60% mole/mole and single-pass saccharide conversion of up to 50%, wherein said values are dependent upon the type of raw material and operational conditions used.

After the dehydration step, 5-HMF undergoes separation using an ion-exchange resin and then directed to the second step, in which 5-HMF is oxidized into 2.5 FDCA.

Therefore. the present invention surpasses the technical advantages of known processes to obtain 2.5 FDCA. since yields for this process are greater than 60%, dependent upon the raw material and operational conditions used and whether the isomerization step is used or not, said yields being greater than those described in the current art, with no need to use solvents during the production step of 5-HMF and not requiring further processes for separation and recovery thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
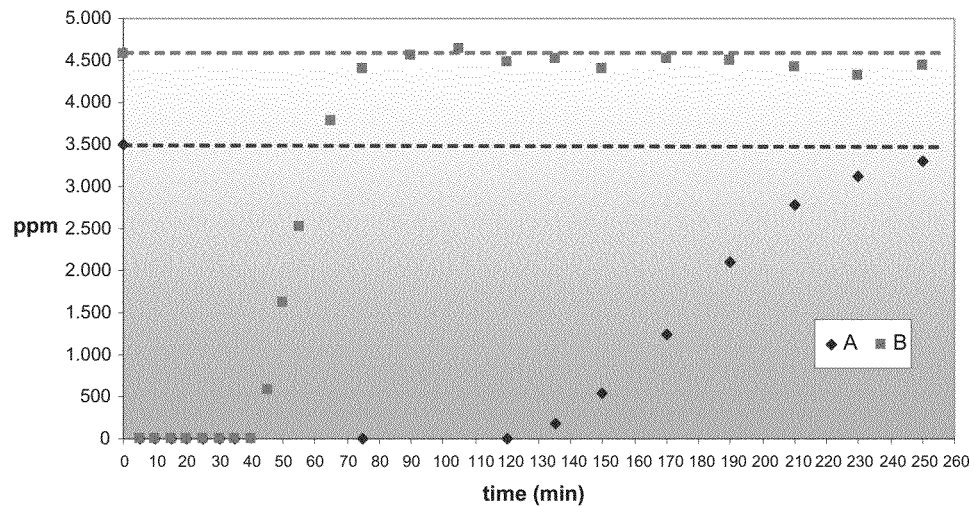
FIG. 1 shows the separation step of 5-HMF via 5-HMF adsorption process in A70 resin exchanged for Ca2+, wherein 5-HMF is shown in the figure as letter A and glucose is shown as letter B.

The producing process for 2.5-FDCA described below refers to loads comprised by aqueous carbohydrate solutions, especially saccharides, such as hexoses (such as, but no limited to, glucose, fructose, levoglucosan), disaccharides (such as sucrose), or even starches. Carbohydrate concentrations in said solutions range from 1% m/m to 50% m/m.

In general, the process involves two steps, a first step wherein 5-HMF in aqueous phase is produced via carbohydrate dehydration, and a second step wherein 5-HMF is oxidized into 2.5-FDCA.

In this case. the step involving dehydration reactions of carbohydrates, especially saccharides, in aqueous phase, the acid function needed for dehydration reactions and also for cleavage reactions is initially performed by H+ ions generated during water dissociation, and later by the organic acids formed during the reaction, especially levulinic and formic acids.

Therefore, the present invention describes an integrated process for producing 2.5 FDCA, wherein said process includes the following steps:

a) introducing a feed stream comprising a carbohydrate-containing aqueous solution at concentrations ranging from 1% to 50% into a reactor operating at temperatures of 150° C. to 300° C., under pressures of 300 psia to 1,800 psia, at spatial velocities of 0.20 to 4h−1, in order to promote a carbohydrate dehydration reaction and formation of 5-HMF;

b) filter the 5-HMF-rich stream obtained in order to remove humins and salts, byproducts generated during the feed dehydration;

c) adjust the pH of the 5-HMF-rich stream that has already been filtered to values between 6.5 and 7.5;

d) have the pH-adjusted, 5-HMF-rich stream that has already been filtered come into contact with an acidic ion-exchange resin with acid site concentration of less than 5.4 eq/g that has been previously exchanged with cations such as Na+, K+, Ca2+(preferably) or other cations, in order to obtain two streams: a first stream containing 5-HMF at concentrations greater than 95%, and a second stream containing unreacted carbohydrates;

e) direct the stream containing unreacted carbohydrates to the dehydration reactor from item a);

f) adjust the pH of the 5-HMF-containing stream to values between 6.5 and 14;

g) have the pH-adjusted, 5-HMF-containing stream come into contact with an air current in a fixed-bed reactor wherein the catalyst is a heterogeneous supported metal catalyst or even a mass metal catalyst, in order to obtain conversions of 5-HMF into 2.5 FDCA greater than 90% mole/mole;

h) recover the 2.5 FDCA produced in g) using precipitation followed by filtration.

During the dehydration step of the process of the present invention, a stream containing 5-HMF and byproducts such as the above-mentioned acids, and also furfural and oligomers (humins), is produced. Separation of byproducts is done by filtering the stream produced during the dehydration step and subsequently removing humins and various salts, and later having the stream from which the humins have already been removed come into contact with an acidic ion-exchange resin that has been previously treated with an alkaline solution, thus obtaining two streams: one 5-HMF-rich stream and one stream rich in unreacted carbohydrates.

During separation and recovery of said 5-HMF-rich stream, the resin bed is fed by a stream containing unreacted carbohydrates (for example, glucose, fructose and levoglucosan), 5-HMF, and other organic compounds generated during the dehydration step, at spatial velocities of 0.5 to 4h−1 at room temperature. During this process, the 5-HMF adsorbed in the resin is later removed using a pure water flow.

Resin beds may operate intermittently such as in a PSA (Pressure Swing Adsorption) system to separate hydrogen or as a simulated moving bed.

After separation, the stream rich in unreacted carbohydrates is returned to the dehydration step, while the 5-HMF-rich stream moves on to the oxidation step.

The 5-HMF-rich stream is cooled down and the pH is adjusted from 6.5 to 14 (preferably), because 5-HMF oxidation can be more readily performed at a pH between 10 and 14. The pH can be adjusted either by using an alkaline solution (such as Na2CO3, Ca(OH)2, NaOH, KOH) or using a basic ion-exchange resin.

During the oxidation step, the pH-corrected, 5-HMF-rich stream is then mixed with an air stream, oxygen-enriched stream, or even pure oxygen, and sent to a fixed-bed reactor with heterogeneous supported metal catalyst such as platinum, palladium, ruthenium, gold, nickel, metal oxides, or a mass metal catalyst such as Raney nickel or Raney copper.

Instead of the fixed-bed reactor, a blending reactor with homogeneous metal catalysts such as noble metal complexes and NHPI/Co(OAc)2/MnOAc2 in acetic acid phase can be used.

The pH is adjusted after the oxidation process to render the solution neutral or acid (pH between 0 and 7), thus allowing precipitation of 2.5 FDCA that was produced. 2.5 FDCA and impurities are filtered out and then rinsed with water. The water in the process returns to be mixed with the aqueous carbohydrate solution that is used as load for the process.

Figure 3:
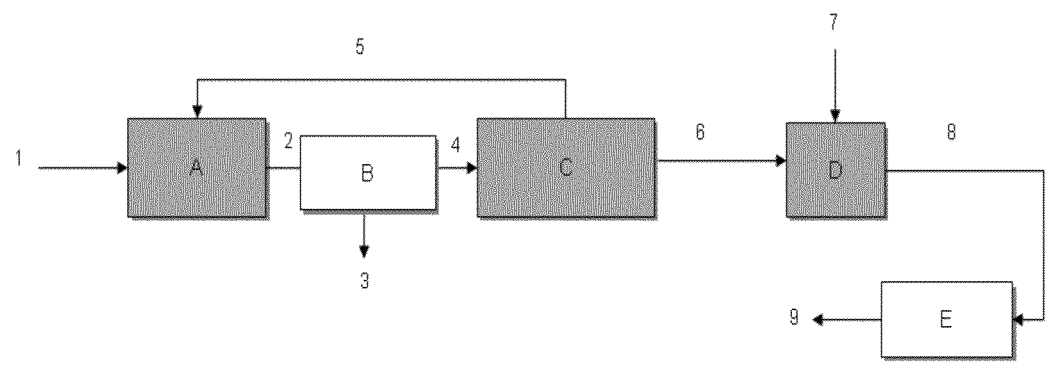
FIG. 3 shows a flow chart of the process for the invention herein.

Assisted by the flow chart in FIG. 3, a preferred embodiment is presented for the 2.5 FDCA integrated production process, as provided by the following steps:
a) a feed stream (1) comprising an aqueous carbohydrate solution is introduced in a reactor (A);
b) the dehydration reaction of the carbohydrates in the feed stream (1) takes place inside the reactor (A) at temperatures of 150° C. to 300° C., pressure of 300 psia to 1.800 psia, and spatial velocities of 0.20 to 4h−1;
c) the 5-HMF-rich stream (2) that leaves the reactor (A) is directed towards a filter (B) where humins and salts are removed by a stream (3), and the pH is adjusted to values from 6.5 to 7.5;
d) the effluent (4) of the filter (B) is then directed toward a column (C) containing an acidic ion-exchange resin that has been previously treated with an alkaline solution, thus obtaining two streams: one 5-HMF-rich stream (6), which after undergoing pH adjustment continues on to the oxidation reactor (D), where the 5-HMF comes into contact with an oxygen-rich stream (7), and a stream rich in unreacted carbohydrates (5) that is recycled into reactor (A); e) the stream (8) containing 2.5-FDA that leaves reactor (D) continues on to a tank (E), where precipitation and filtration take place to recover a 2.5-FDCA-rich stream.

Figure 4:
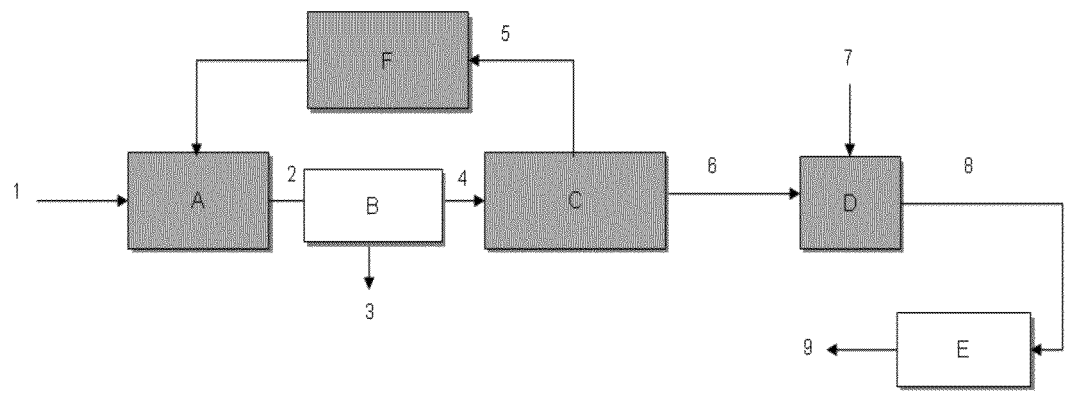
FIG. 4 shows a flow chart of the process for the invention herein, comprising the additional step of isomerization when aqueous sucrose solutions are used as load for the process.

The 2.5 FDCA production process described herein may optionally have an isomerization step. Said process is illustrated in the flow chart in FIG. 4, comprised by the same elements (streams, reactors, filters, etc.) as indicated in FIG. 3, and the only difference between the two flow charts is that instead of being recycled into the dehydration reactor (A), the stream containing unreacted carbohydrates (5) is sent to an isomerization reactor (F). This optional step is used when a solution containing sucrose, glucose, levoglucosan, or starch (glucose+fructose) is used as the stream feed for the process.

Introducing an isomerization step after dehydration occurs because fructose has more selectivity when producing 5-HMF when compared to glucose, since glucose is more chemically stable. Therefore, sucrose, formed by two molecules, one glucose and one fructose; levoglucosan, which hydrates glucose before being dehydrated into 5-HMF; starch, which is cleaved into many glucose molecules in the dehydration reactor; and glucose itself, after separation in an ion-exchange resin bed, are partially isomerized into fructose (limited to thermodynamic balance), thus increasing overall 5-HMF yield.

If, for example, the process operates using sucrose as a load and without the isomerization step, fructose is preferably consumed in the dehydration reaction, which makes the stream containing unreacted carbohydrates to have a higher glucose concentration than a fructose concentration. This stream, which originates from the 5-HMF separation and recovery step when directly fed into the reactor with the load containing sucrose only, causes a drop in overall fructose concentration in the phase, which translates into a drop in selectivity and 5-HMF yield.

Using the additional isomerization step, it is possible to increase fructose concentration in the stream coming from the 5-HMF separation and recovery step, since glucose isomerization generates fructose. By using the additional isomerization step, the fructose concentration in the dehydration reactor becomes close to the thermodynamic balance concentration, which is approximately 50% mole/mole, and the levels of selectivity and single-pass conversion for the overall dehydration process can be maintained.

In this case, isomerization could be done using an enzymatic process, with the help of isomerases, or using a chemical process, with the help of basic catalysts.

The following examples are meant to illustrate the 2.5-FDCA integrated production process, but in no way to limit, the present invention.

EXAMPLE 1

This example illustrates the separation and recovery of 5-HMF from a stream formed by glucose aqueous solution containing 5-HMF.

30 mL Amberlyst 70 resin was rinsed with 500 mL milliQ water. After this procedure, 400 mL of 5% CaCl2 m/m solution was percolated, followed by a new rinse with 500 mL milliQ water.

After the resin preparation process, an aqueous solution containing 4630 ppm glucose and 3174 ppm 5-HMF was percolated at a spatial velocity of 1h−1 at 25° C., with samples collected every 5 minutes (FIG. 1). After saturation of the bed, milliQ water was percolated in the same direction as the previous flow at spatial velocity of 1h−1 at 25° C., with samples also collected every 5 minutes (FIG. 2).

Tests were performed using a high performance chromatography Agilent 1260 with Diode Array Detector (DAD) and Evaporative Light Scattering Detector (ELSD). A Zorbax Eclipse plus C18 (4.6×100 mm 3.5 micra) column was used to detect 5-HMF and a Zorbax Carbohydrate column (4.6×250 mm 5 micra) column was used to detect glucose.

Figure 2:
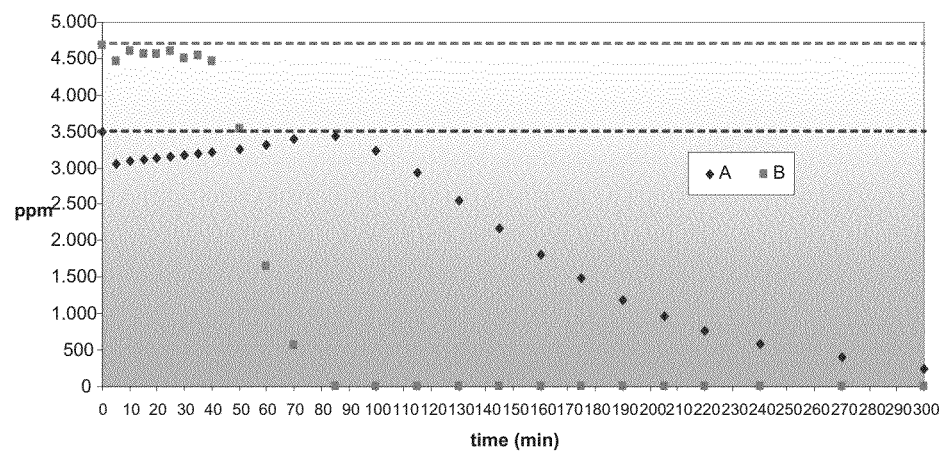
FIG. 2 shows the recovery step of 5-HMF via desorption of 5-HMF with water in A70 resin exchanged for Ca2+, wherein 5-HMF is shown in the figure as letter A and glucose is shown as letter B.

As seen in FIG. 1, the bed effluent was formed by aqueous solution with 100% m/m glucose (dry base) from 40 minutes to 130 minutes, while FIG. 2 shows that the bed effluent was formed by aqueous solution with 100% m/m 5-HMF (dry base) beginning at the 90-minute mark. The mass balance error was 0.5% m/m for 5-HMF and 8.3% for glucose.

EXAMPLE 2

This example illustrates preparation of 5-HMF by dehydrating a stream comprised by a 10% aqueous sucrose solution using sub-critical water as a catalyst.

150 mL of milliQ water that had previously undergone ultrasonic degassing for 20 minutes and N2 bubbling for 30 minutes was warmed to 180° C. in a stainless steel reactor with mechanical agitation with enough pressure to keep the system in the liquid phase. 40 mL of 50% m/m sucrose solution was injected after the temperature was stabilized, followed by 10 mL milliQ water at a rate of 10 mL/min. The reaction was started at the end of the injection (t=0).

After 30 minutes, the reactor effluent was filtered and analyzed by HPLC Agilent 1260 with DAD and ELSD detectors. Saccharides were determined by ELSD detector and Zorbax Carbohydrate (4.6×250 mm 5 micra) column, while furanic compounds and organic acids were determined using a Zorbax Eclipse plus C18 (4.6×100 mm 3.5 micra) column and a DAD (210 nm and 280 nm) detector.

Sucrose conversion during that time was complete. Conversion of generated saccharides was indicated as overall conversion:

$$X_{global} = \frac{(n_{sucrose})_{input} - (n_{glucose} + n_{fructose} + n_{levoglucosan})_{output}}{(n_{sucrose})_{input}}$$

Yield and selectivity for 5-HMF were defined as:

$$Y_{HMF} = \frac{(n_{HMF})_{output}}{(n_{sucrose})_{input}}$$

$$S_{HMF} = \frac{Y_{HMF}}{X_{global}}$$

After 30 minutes into the reaction, a 5-HMF selectivity of 78.1% mole/mole was achieved, with an overall conversion of 30.1% mole/mole. Conversion of the generated fructose was 58.0% mole/mole.

As mentioned before, an increase in the glucose input concentration will occur if the unreacted saccharides are directly fed back into the dehydration reactor after being separated using the procedure described in Example 1, resulting in lower 5-HMF yields. However, if the saccharide current is isomerized before being sent to the dehydration reactor, overall 5-HMF yields will be kept at a 78% level.

EXAMPLE 3

This example illustrates preparation of 5-HMF by dehydrating a stream comprised by a 10% aqueous glucose solution using sub-critical water as a catalyst.

150 mL of milliQ water that had previously undergone ultrasonic degassing for 20 minutes and N2 bubbling for 30 minutes was warmed to 190° C. in a stainless steel reactor with mechanical agitation with enough pressure to keep the system in the liquid phase. 40 mL of 50% m/m glucose solution was injected after the temperature was stabilized, followed by 10 mL milliQ water at a rate of 10 mL/min. The reaction was started at the end of the injection (t=0).

After 45 minutes, the reactor effluent was filtered and analyzed by HPLC Agilent 1260 with DAD and ELSD detectors. Saccharides were determined by ELSD detector and Zorbax Carbohydrate (4.6×250 mm 5 micra) column, while furanic compounds and organic acids were determined using a Zorbax Eclipse plus C18 (4.6×100 mm 3.5 micra) column and a DAD (210 nm and 280 nm) detector.

Since a portion of the glucose is converted into levoglucosan and a portion is isomerized into fructose, conversion of generated saccharides was indicated as overall conversion:

$$X_{global} = \frac{(n_{glucose})_{input} - (n_{glucose} + n_{fructose} + n_{levoglucosan})_{output}}{(n_{glucose})_{input}}$$

Yield and selectivity for 5-HMF were defined as:

$$Y_{HMF} = \frac{(n_{HMF})_{output}}{(n_{glucose})_{input}}$$

$$S_{HMF} = \frac{Y_{HMF}}{X_{global}}$$

After 45 minutes into the reaction, a 5-HMF selectivity of 71.3% mole/mole was achieved, with an overall conversion of 15.8% mole/mole. No formation of fructose was observed under said operational conditions.

The process can be kept operating at an overall yield near the single-pass selectivity levels reached when sucrose was used as load, by separating glucose and unreacted levoglucosan from the 5-HMF formed using the process described in Example 1 and by having this saccharide current undergo isomerization until almost reaching thermodynamics balance condition before it is fed back, as long as the operation conditions are adjusted for this case.

EXAMPLE 4

This example illustrates preparation of 5-HMF by dehydrating a stream comprising a 10% aqueous levoglucosan solution using sub-critical water as a catalyst.

150 mL of milliQ water that had previously undergone ultrasonic degassing for 20 minutes and N2 bubbling for 30 minutes was warmed to 190° C. in a stainless steel reactor with mechanical agitation with enough pressure to keep the system in the liquid phase. 40 mL of 50% m/m levoglucosan solution was injected after the temperature was stabilized, followed by 10 mL milliQ water at a rate of 10 mL/min. The reaction was started at the end of the injection (t=0).

After 40 minutes, the reactor effluent was filtered and analyzed by HPLC Agilent 1260 with DAD and ELSD detectors. Saccharides were determined by ELSD detector and Zorbax Carbohydrate (4.6×250 mm 5 micra) column, while furanic compounds and organic acids were determined using a Zorbax Eclipse plus C18 (4.6×100 mm 3.5 micra) column and a DAD (210 nm and 280 nm) detector.

Since not all of the levoglucosan is converted into glucose and since a portion of the generated glucose is isomerized into fructose, conversion of generated saccharides was indicated as overall conversion:

$$X_{global} = \frac{(n_{levoglucosan})_{input} - (n_{glucose} + n_{fructose} + n_{levoglucosan})_{output}}{(n_{levoglucosan})_{input}}$$

Yield and selectivity for 5-HMF were defined as:

$$Y_{HMF} = \frac{(n_{HMF})_{output}}{(n_{levoglucosan})_{input}}$$

$$S_{HMF} = \frac{Y_{HMF}}{X_{global}}$$

After 40 minutes into the reaction, a 5-HMF selectivity of 82.6% mole/mole was achieved, with an overall conversion of 2.8% mole/mole. No formation of fructose was observed under said operational conditions.

The process can be kept operating at an overall yield near the single-pass selectivity levels reached when sucrose was used as load, by separating glucose and unreacted levoglucosan from the 5-HMF formed using the process described in Example 1 and by having this saccharide stream undergo isomerization until almost reaching thermodynamics balance condition before it is fed back, as long as the operation conditions are adjusted for this case.

EXAMPLE 5

This example illustrates preparation of 5-HMF by dehydrating a stream comprising a 10% aqueous fructose solution using sub-critical water as a catalyst.

150 mL of milliQ water that had previously undergone ultrasonic degassing for 20 minutes and N2 bubbling for 30 minutes was warmed to 170° C. in a stainless steel reactor with mechanical agitation with enough pressure to keep the system in the liquid phase. 40 mL of 50% m/m fructose solution was injected after the temperature was stabilized, followed by 10 mL milliQ water at a rate of 10 mL/min. The reaction was started at the end of the injection (t=0).

After 30 minutes, the reactor effluent was filtered and analyzed by HPLC Agilent 1260 with DAD and ELSD detectors. Saccharides were determined by ELSD detector and Zorbax Carbohydrate (4.6×250 mm 5 micra) column, while furanic compounds and organic acids were determined using a Zorbax Eclipse plus C18 (4.6×100 mm 3.5 micra) column and a DAD (210 nm and 280 nm) detector.

Since a small portion of the fructose is isomerized into glucose and since a portion of said glucose forms levoglucosan, conversion of generated saccharides was indicated as overall conversion:

$$X_{global} = \frac{(n_{fructose})_{input} - (n_{glucose} + n_{fructose} + n_{levoglucosan})_{output}}{(n_{fructose})_{input}}$$

Yield and selectivity for 5-HMF were defined as:

$$Y_{HMF} = \frac{(n_{HMF})_{output}}{(n_{fructose})_{input}}$$

$$S_{HMF} = \frac{Y_{HMF}}{X_{global}}$$

After 30 minutes into the reaction, a 5-HMF selectivity of 82.3% mole/mole was achieved, with an overall conversion of 29.8% mole/mole. No formation of glucose or levoglucosan was observed under said operational conditions.

The overall process yield can be kept at the same single-pass selectivity levels of 82% mole/mole by separating unreacted fructose from 5-HMF formed using the process described in Example 1 and looping it back to reenter the reactor.

What is claimed is:

1. 2.5-FURANDICARBOXYLIC ACID INTEGRATED PRODUCTION PROCESS comprising the following steps:
   a) introducing a feed stream comprising a carbohydrate-containing aqueous solution at concentrations ranging from 1% to 50% in a reactor operating at temperatures of 150° C. to 300° C., under pressures of 300 psia to 1,800 psia, at spatial velocities of 0.20 to 4h−1, in order to promote a carbohydrate dehydration reaction and formation of 5-HMF, with selectivity greater than 60% mole/mole;
   b) filter the 5-HMF-rich stream obtained in order to remove humins and salts, byproducts generated during the feed dehydration;
   c) adjust the pH of the 5-HMF-rich stream that has already been filtered to values between 6.5 and 7.5;
   d) have the pH-adjusted, 5-HMF-rich stream that has already been filtered come into contact with an acidic ion-exchange resin that has been previously exchanged with cations such as Na+, K+, Ca2+(preferably) or other cations, in order to obtain two streams: a first stream containing 5-HMF at concentrations greater than 90%, and a second stream containing unreacted carbohydrates;
   e) direct the stream containing unreacted carbohydrates to the dehydration reactor from item a);
   f) adjust the pH of the 5-HMF-containing stream to values between 6.5 and 14;
   g) have the pH-adjusted, 5-HMF-containing stream come into contact with an oxygen-rich stream in a fixed-bed reactor, wherein the catalyst is a heterogeneous supported metal catalyst or even a mass metal catalyst, in order to obtain conversions of 5-HMF into 2.5 FDCA greater than 90% mole/mole;
   h) recover the 2.5-FDCA produced in g) using precipitation followed by filtration.

2. The PROCESS of claim 1, wherein the carbohydrate is a saccharide.

3. The PROCESS of claim 1, wherein the saccharide is a disaccharide.

4. The PROCESS of claim 1, wherein the disaccharide is sucrose.

5. The PROCESS of claim 1, wherein the saccharide is an hexose.

6. The PROCESS of claim 1, wherein the carbohydrate is obtained by biomass pyrolysis.

7. The PROCESS of claim 1, wherein the carbohydrate is levoglucosan.

8. The PROCESS of claim 1, wherein the carbohydrate is starch.

9. The PROCESS of claim 1, wherein the acid site concentration of the acidic ion-exchange resin used in step d) is less than 5.4 eq/g.

10. The PROCESS in claim 1, wherein the process comprises an additional isomerization step after step d) wherein the stream thereby produced is redirected to the reactor in step a).

* * * * *